United States Patent
Maruyama et al.

(10) Patent No.: US 9,265,417 B2
(45) Date of Patent: Feb. 23, 2016

(54) SLIT LAMP MICROSCOPE

(71) Applicant: Takagi Seiko Co., Ltd., Nakano-shi, Nagano (JP)

(72) Inventors: Takahiro Maruyama, Nakano (JP); Takeshi Nara, Nakano (JP); Shigeo Kanazawa, Nakano (JP)

(73) Assignee: Takagi Seiko Co., Ltd., Nagano (JP)

( * ) Notice: Subject to any disclaimer, the term of this patent is extended or adjusted under 35 U.S.C. 154(b) by 131 days.

(21) Appl. No.: 14/041,937

(22) Filed: Sep. 30, 2013

(65) Prior Publication Data

US 2014/0211163 A1 Jul. 31, 2014

(30) Foreign Application Priority Data

Jan. 31, 2013 (JP) .................................. 2013-017315

(51) Int. Cl.
 *A61B 3/00* (2006.01)
 *A61B 3/10* (2006.01)
 *A61B 3/135* (2006.01)

(52) U.S. Cl.
 CPC ...................................... *A61B 3/135* (2013.01)

(58) Field of Classification Search
 USPC ......... 351/200, 205, 204, 206, 214, 210, 221, 351/222, 245, 243, 246
 See application file for complete search history.

(56) References Cited

U.S. PATENT DOCUMENTS 5,780,174 A * 7/1998 Tokito et al. .................. 428/690

FOREIGN PATENT DOCUMENTS

| JP | 2002-102173 A | 4/2002 |
| JP | 2011-177273 A | 9/2011 |

* cited by examiner

*Primary Examiner* — Joseph P Martinez
*Assistant Examiner* — Brandi Thomas
(74) *Attorney, Agent, or Firm* — Birch, Stewart, Kolasch & Birch, LLP (57) ABSTRACT

The slit lamp microscope is capable of easily adjusting a slit-light and a backlight. The slit lamp microscope comprises: a slit lamp for emitting a slit-light; a mirror unit having a reflecting mirror or a prism, which reflects the slit-light emitted from the slit lamp toward an eye of an examinee; a microscope unit for observing the eye of the examinee; and a backlight source for emitting a backlight, which illuminates a circumference of the slit-light, toward the eye of the examinee. The backlight source is provided to the mirror unit.

7 Claims, 9 Drawing Sheets

SLIT LAMP MICROSCOPE

CROSS-REFERENCE TO RELATED APPLICATION

This application is based upon and claims the benefit of priority of the prior Japanese Patent Application No. P2013-017315, filed on Jan. 31, 2013, and the entire contents of which are incorporated herein by reference.

FIELD

The present invention relates to a slit lamp microscope for observing an eye of an examinee with a slit lamp.

BACKGROUND

A slit lamp microscope is used, by an ophthalmologist, for observing an eye of an examinee.

A conventional slit lamp microscope will be explained.

The slit lamp microscope irradiates an eye of an examinee with a slit-light from an oblique direction so as to visualize and observe transparent or semi-transparent tissues. The slit lamp microscope includes a slit-light optical system for emitting the slit-light and a microscope unit.

In case of irradiating the eye of the examinee with the slit-light only, an irradiation point on the eye is sometimes unknown. In this state, if a picture of the eye is taken, the slit-light will be focused on a slit. To solve this problem, a backlight source for illuminating a circumference of the slit-light, is provided to the conventional slit lamp microscope.

Japanese Laid-open Patent Publication No. 2011-177273 discloses a light emitting diode (LED) used for emitting a backlight. An auxiliary lamp unit including the LED is attached to a front end of a flexible arm.

The flexible arm is attached to a face supporting section, which supports a face of the examinee, and the backlight is emitted from a position above the eye of the examinee.

In the slit lamp microscope disclosed in Japanese Laid-open Patent Publication No. 2011-177273, the slit-light optical system for emitting the slit-light and the auxiliary lamp unit for emitting the backlight are separately provided.

However, in the conventional slit lamp microscope, irradiation points of the slit-light and the backlight on the eye of the examinee are separately adjusted when the slit-light and the backlight are emitted. So it takes a long time to adjust the both irradiation points.

SUMMARY

Accordingly, it is an object to provide a slit lamp microscope capable of solving the above described problem of the conventional slit lamp microscope. Namely, the slit lamp microscope of the present invention is capable of easily adjusting a slit-light and a backlight.

To achieve the object, the present invention has following structures.

Namely, the slit lamp microscope of the present invention comprises:
a slit lamp for emitting a slit-light;
a mirror unit having a reflecting mirror or a prism, which reflects the slit-light emitted from the slit lamp toward an eye of an examinee;
a microscope unit for observing the eye of the examinee; and
a backlight source for emitting a backlight, which illuminates a circumference of the slit-light, toward the eye of the examinee, and
the backlight source is provided to the mirror unit.

With this structure, when the mirror unit is adjusted, an angle and a position of the backlight can be simultaneously adjusted. Therefore, the slit-light and the backlight can be easily adjusted in a short time.

In the slit lamp microscope, the backlight source may be provided in a lower part of the reflecting mirror or the prism of the mirror unit.

With this structure, the backlight is emitted, toward the eye of the examinee, from a position under the slit-light, so that glare given to the examinee can be reduced.

In the slit lamp microscope, the backlight source may be provided in an upper part of the reflecting mirror or the prism of the mirror unit.

In the slit lamp microscope, an outer wall of the mirror unit may be made of a metal, and heat generated by the backlight source may be released outside from the outer wall of the mirror unit.

With this structure, the heat generated by the backlight source can be sufficiently released outside, so an independent heat-releasing member is not required.

In the slit lamp microscope of the present invention, the slit-light and the backlight can be easily adjusted.

BRIEF DESCRIPTION OF THE DRAWINGS

Embodiments of the present invention will now be described by way of examples and with reference to the accompanying drawings, in which.

DETAILED DESCRIPTION OF THE EMBODIMENT

Preferred embodiments of the present invention will now be described in detail with reference to the accompanying drawings.

First Embodiment

Figure 1:
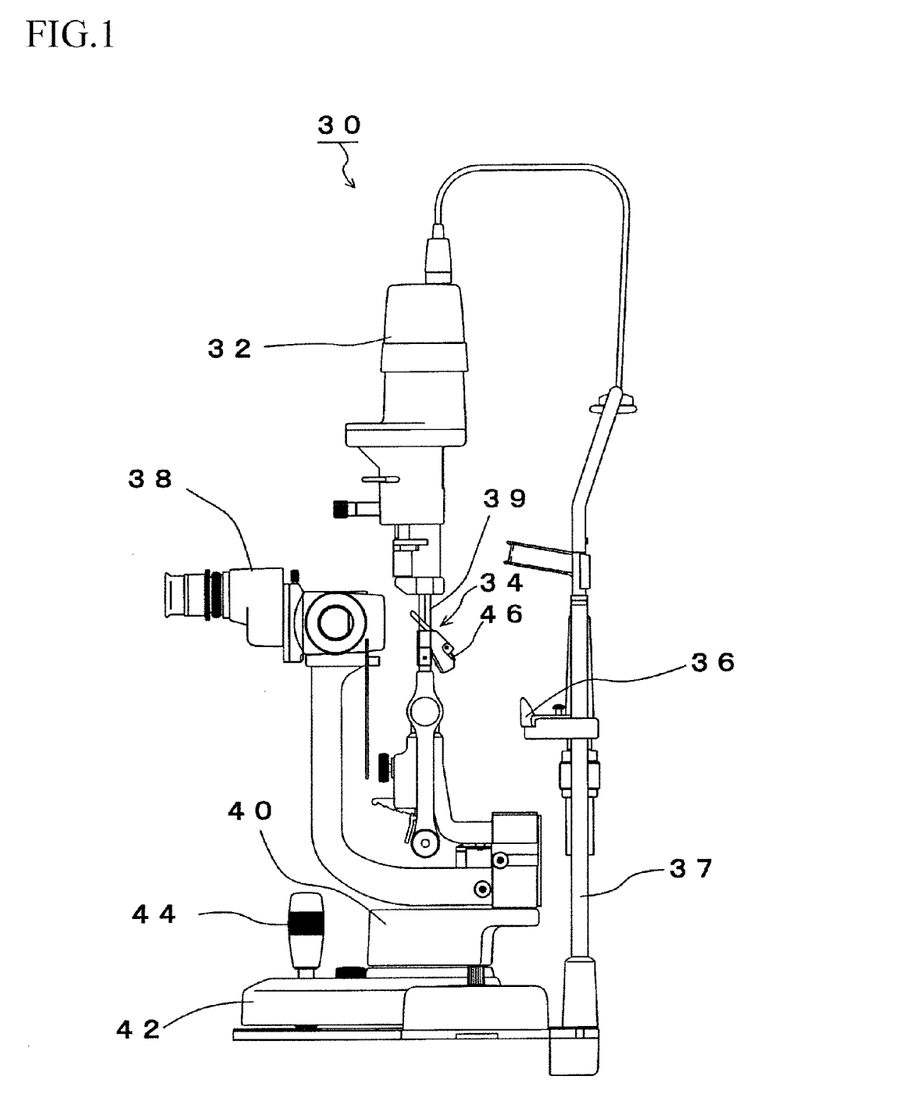
FIG. 1 is a side view of a slit lamp microscope of a first embodiment, which shows a whole structure.
Figure 2:
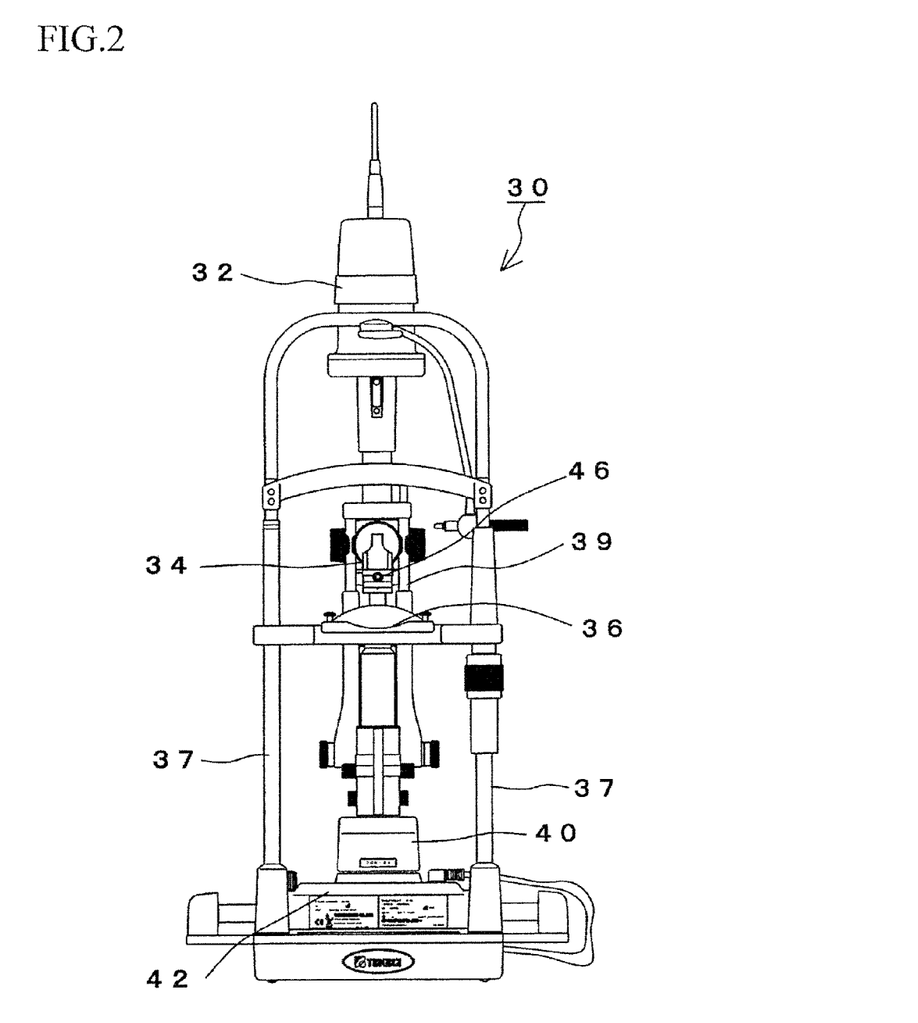
FIG. 2 is a front view of the slit lamp microscope of the first embodiment, which shows the whole structure seen from an examinee side.

A whole structure of a slit lamp microscope 30 of a first embodiment is shown in FIGS. 1 and 2.

The slit lamp microscope 30 includes a slit lamp 32 for emitting a slit-light, and a mirror unit 34 for reflecting the slit-light emitted from the slit lamp 32 toward an eye of an examinee In the present embodiment, the slit lamp 32 emits the slit-light downward, and the mirror unit 34 is provided under the slit lamp 32. Note that, the slit lamp 32 has a known inner structure, so detailed explanation will be omitted.

The slit lamp 32 and the mirror unit 34 are connected to each other by a pair of connection arms 39.

A backlight source 46, which illuminates a circumference of the slit-light, is integrated with the mirror unit 34.

A chin supporting section 36, on which a chin of the examinee will be mounted, is provided to the slit lamp microscope 30. The chin supporting section 36 is provided between two supporting arms 37, which are extended in the vertical direction.

A microscope 38, which is used for observing an eye of the examinee whose chin has been mounted on the chin supporting section 36, is located to face the chin supporting section 36. Note that, an imaging unit, e.g., camera, may be attached to the microscope 38.

The microscope 38 is attached to a support base 40. The slit lamp 32 and the mirror unit 34, which are connected to each other by the connection arms 39, are also attached to the support base 40. The support base 40 is provided on a mounting member 42 and capable of finely moving. Therefore, the microscope 38, the slit lamp 32 and the mirror unit 34 and can be finely moved, with respect to the mounting member 42, by the fine motion of the support base 40.

On the other hand, the supporting arms 37, which support the chin supporting section 36, are immovably fixed. Therefore, the support base 40 can be moved with respect to the eye of the examinee, and an irradiation point of the slit-light on the eye of the examinee can be adjusted.

The fine motion of the support base 40 can be manually controlled by a control stick 44.

Figure 3:
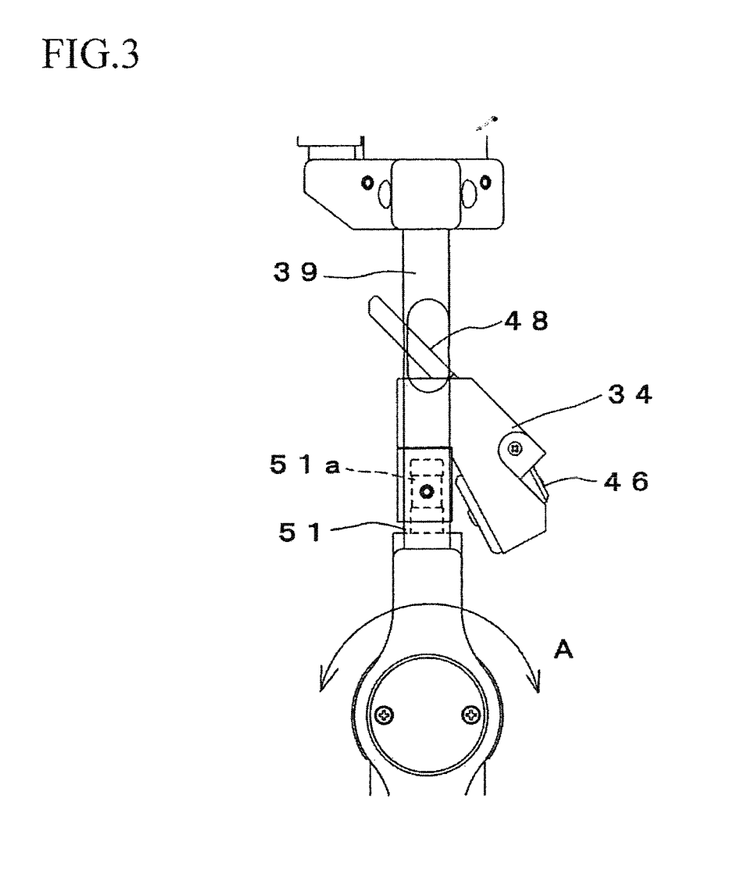
FIG. 3 is a left side view of a mirror unit of the slit lamp microscope of the first embodiment, which is seen from the examinee.
Figure 4:
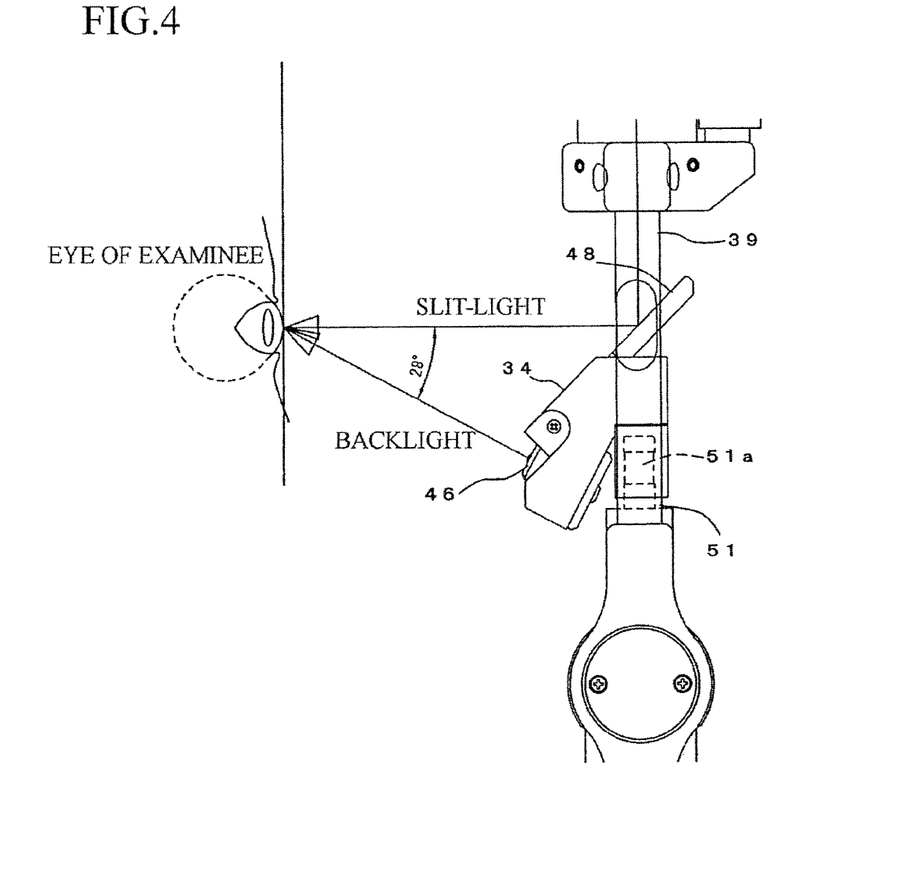
FIG. 4 is a right side view of the mirror unit of the slit lamp microscope of the first embodiment, which is seen from the examinee.
Figure 5:
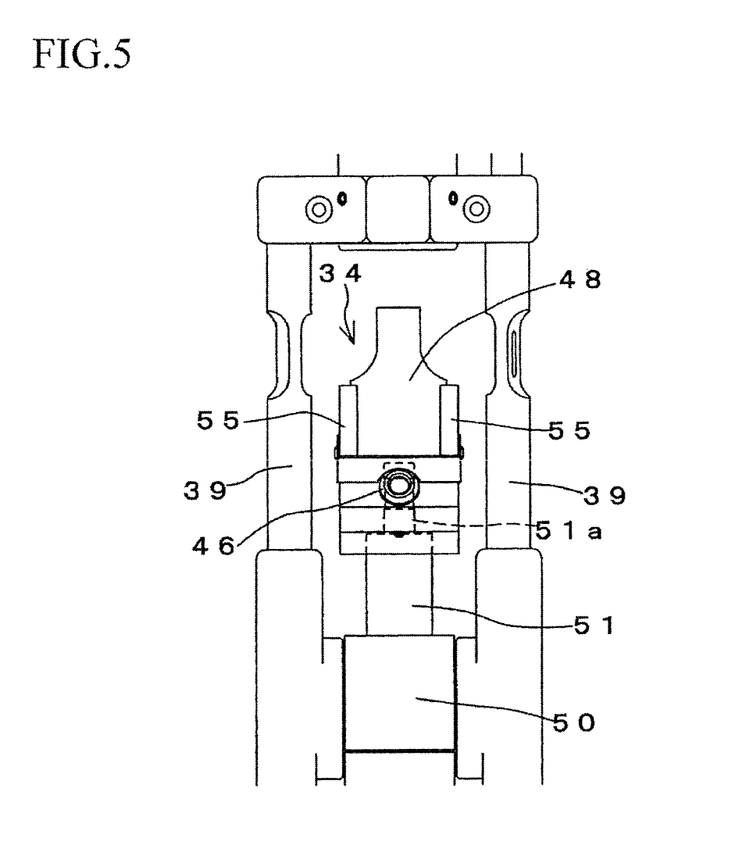
FIG. 5 is a front view of the mirror unit of the slit lamp microscope of the first embodiment, which is seen from the examinee side.
Figure 6:
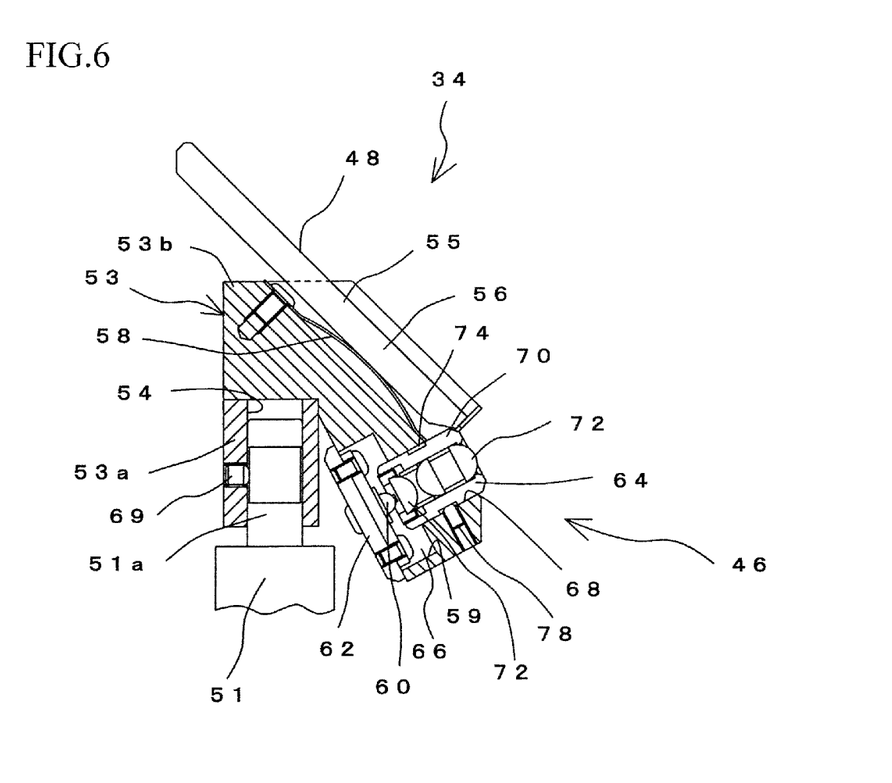
FIG. 6 is a left side view of the mirror unit of the slit lamp microscope of the first embodiment, which shows an inner structure seen from the examinee.

Next, a structure of the mirror unit 34 will be explained with reference to FIGS. 3-6. FIG. 3 is a left side view of a mirror unit of the slit lamp microscope of the first embodiment, which is seen from the examinee, and FIG. 4 is a right side view of the mirror unit of the slit lamp microscope of the first embodiment, which is seen from the examinee. FIG. 5 is a front view of the mirror unit of the slit lamp microscope of the first embodiment, which is seen from the examinee side, and FIG. 6 is a left side view of the mirror unit of the slit lamp microscope of the first embodiment, which shows an inner structure seen from the examinee.

The mirror unit 34 has a reflecting mirror 48 which is set to face the eye of the examinee. The reflecting mirror 48 is inclined 45 degrees with respect to a light path of the slit-light, which is emitted in the vertical direction from the slit lamp 32, so as to irradiate the eye of the examinee with the slit-light.

The mirror unit 34 has a backlight source 46. The backlight source 46 emits a backlight toward the eye of the examinee as well as the slit-light.

In the present embodiment, the backlight source 46 is provided in a lower part of the reflecting mirror 48. The backlight source 46 emits the backlight, toward the eye, from a position under a horizontal plane including the eye. A light path of the backlight is inclined 28 degrees with respect to the horizontal plane including the eye, and the backlight is emitted toward the eye of the examinee from underneath.

By emitting the backlight toward the eye of the examinee from the lower position at said angle, glare of the backlight given to the examinee can be reduced.

The mirror unit 34 is attached to a holding member 51, which is provided between the connection arms 39. An upper end of the holding member 51 is connected to the mirror unit 34, and a lower end thereof is connected to a connection member 50. The connection member 50 is horizontally spanned between the connection arms 39.

The connection member 50 is attached to the two connection arms 39 by a horizontal rotary shaft (not shown), so that the connection member 50 can be rotated, in a direction indicated by an arrow A shown in FIG. 3, about the horizontal rotary shaft. By rotating the connection member 50 about the horizontal rotary shaft, the angle of the mirror unit 34 connected to an upper part of the connection member 50, in the upper and the lower directions, can be adjusted.

An upper part 51a of the holding member 51 is formed into a columnar shape, and the upper part 51a is inserted in the mirror unit 34. The mirror unit 34 is capable of rotating about the vertical upper part 51a of the holding member 51. By rotating the connection member 50 about an vertical axis, the angle of the mirror unit 34 in the horizontal direction can be adjusted.

By the above described structure, the angle of the mirror unit 34 in the upper direction, the lower direction and the horizontal direction can be adjusted. The mirror unit 34 includes the reflecting mirror 48 and the backlight source 46, so that the angle of the slit-light reflected by the reflecting mirror 48 and the angle of the backlight can be simultaneously adjusted by adjusting the angle of the mirror unit 34. Namely, the angle of the slit-light and the angle of the backlight need not be separately adjusted, so that the operation can be easily performed.

Successively, an inner structure of the mirror unit 34 will be explained.

The mirror unit 34 has a metal chassis 53, in which the reflecting mirror 48 and the backlight source 46 are accommodated.

The metal chassis 53 has: a base section 53a having a hole 54, in which the upper part 51a of the holding member 51 is inserted; and a main body section 53b, to which the reflecting mirror 48 and the backlight source 46 are attached.

A fixing screw 69, which is capable of tightening the upper part 51a of the holding member 51 from outside of the chassis 53, is provided to the base section 53a of the chassis 53. A front end of the fixing screw 69 contacts the upper part 51a of the holding member 51. By tightening the fixing screw 69, a heading of the chassis 53 in the horizontal direction can be fixed.

Holding sections 55, which clamp side edges of the reflecting mirror 48 so as to attach the reflecting mirror 48, are provided to the main body section 53b of the chassis 53. Each of the holding sections 55 has a groove 56 whose width is nearly equal to that of a thickness of the reflecting mirror 48. With this structure, the reflecting mirror 48 can be slid in the grooves 56 and clamped between the holding sections 55.

A spring member 58 is provided on the rear side of the reflecting mirror 48 and between the holding sections 55 so as to press a rear face of the reflecting mirror 48. By the spring member 58, the reflecting mirror 48 is pressed toward the front side and fixed between the holding sections 55 without play.

A mounting section 59, to which the backlight source 46 is attached, is provided under the holding sections 55 of the main body section 53b of the chassis 53. Further, in the present embodiment, the backlight source 46 includes an LED board 62, on which an LED 60 is mounted, and a lens unit 64 having a plurality of lenses 72. The LED 60 emits the backlight. A concave section 66, which is concaved from the rear side toward the front side, is formed in the main body section 53b of the chassis 53. The LED board 62 is attached into the concave section 66 from the rear side.

A communication hole 68, which communicates the concave section 66 to the front side of the chassis 53, is formed in the main body section 53b of the chassis 53. The lens unit 64 is fitted in the communication hole 68. The lens unit 64 has a tubular member 70, in which the lenses 72 are assembled. A groove 74 is formed in an outer circumferential face of the tubular member 70. A front end of a fixing screw 78 contacts the groove 74, and the fixing screw 78 can be tightened from outside of the chassis 53. By tightening the fixing screw 78, the tubular member 70 is fixed in the communication hole 68.

The light of the LED 60 on the LED board 62 passes through the lenses 72 and is emitted from the front side of the chassis 53. The light is emitted toward the eye of the examinee as the backlight.

Since the backlight source 46 is accommodated in the chassis 53 to which the reflecting mirror 48 is attached, heat generated in the LED board 62 can be conducted to the metal chassis 53 and released outside from an outer wall of the chassis 53. In the conventional slit lamp microscope, an independent heat-releasing means for releasing the heat generated in the backlight source is required. On the other hand, in the present embodiment, the heat generated in the backlight source 46 can be easily released without any special means.

Second Embodiment

Figure 7:
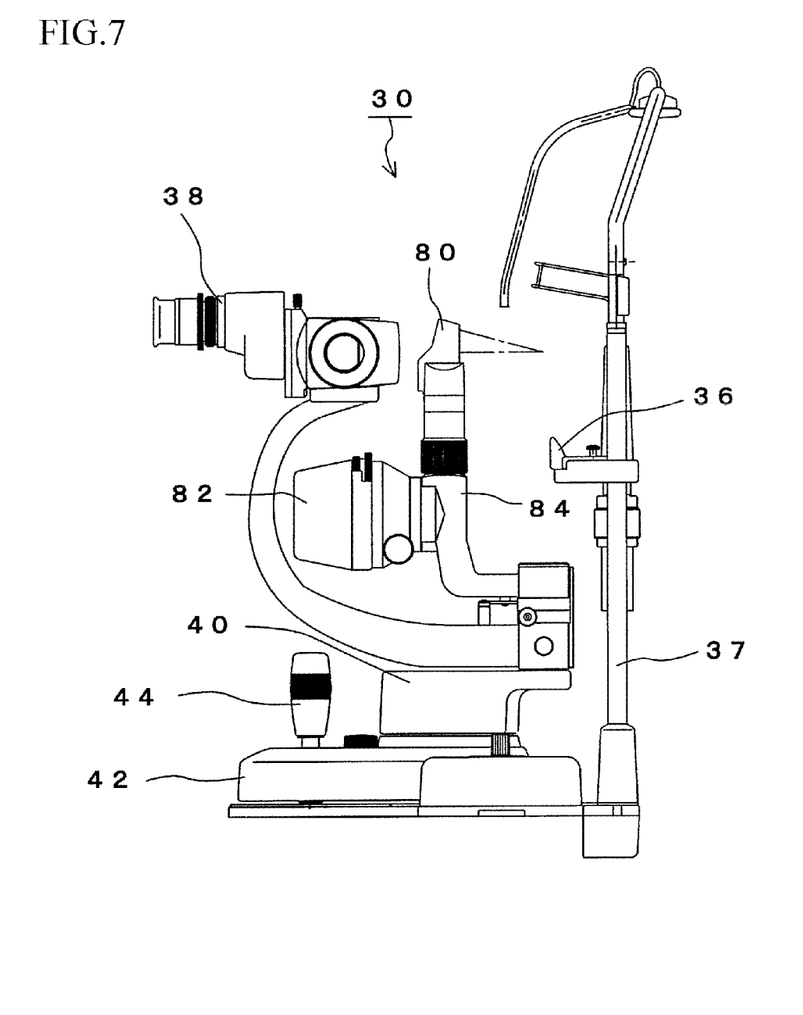
FIG. 7 is a side view of a slit lamp microscope of a second embodiment, which shows a whole structure.
Figure 8:
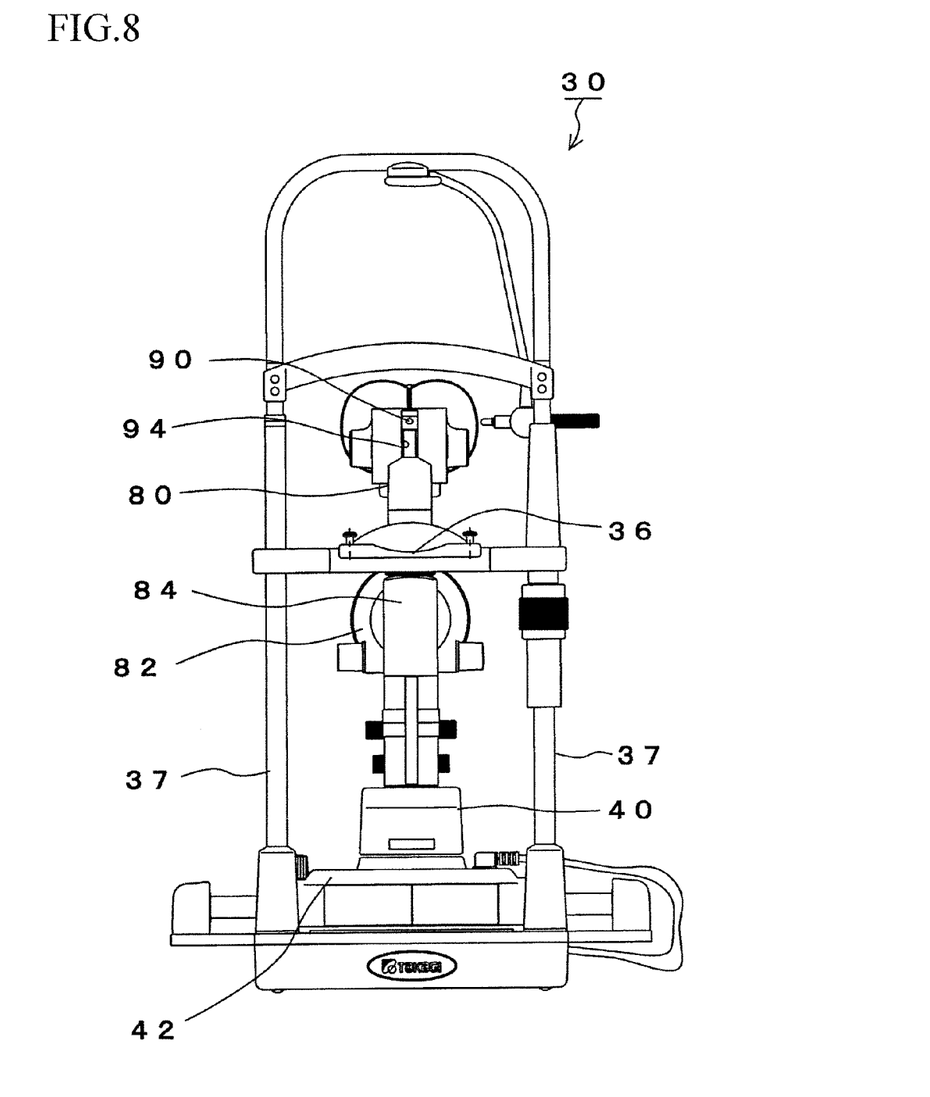
FIG. 8 is a front view of the slit lamp microscope of the second embodiment, which shows the whole structure seen from the examinee side.
Figure 9:
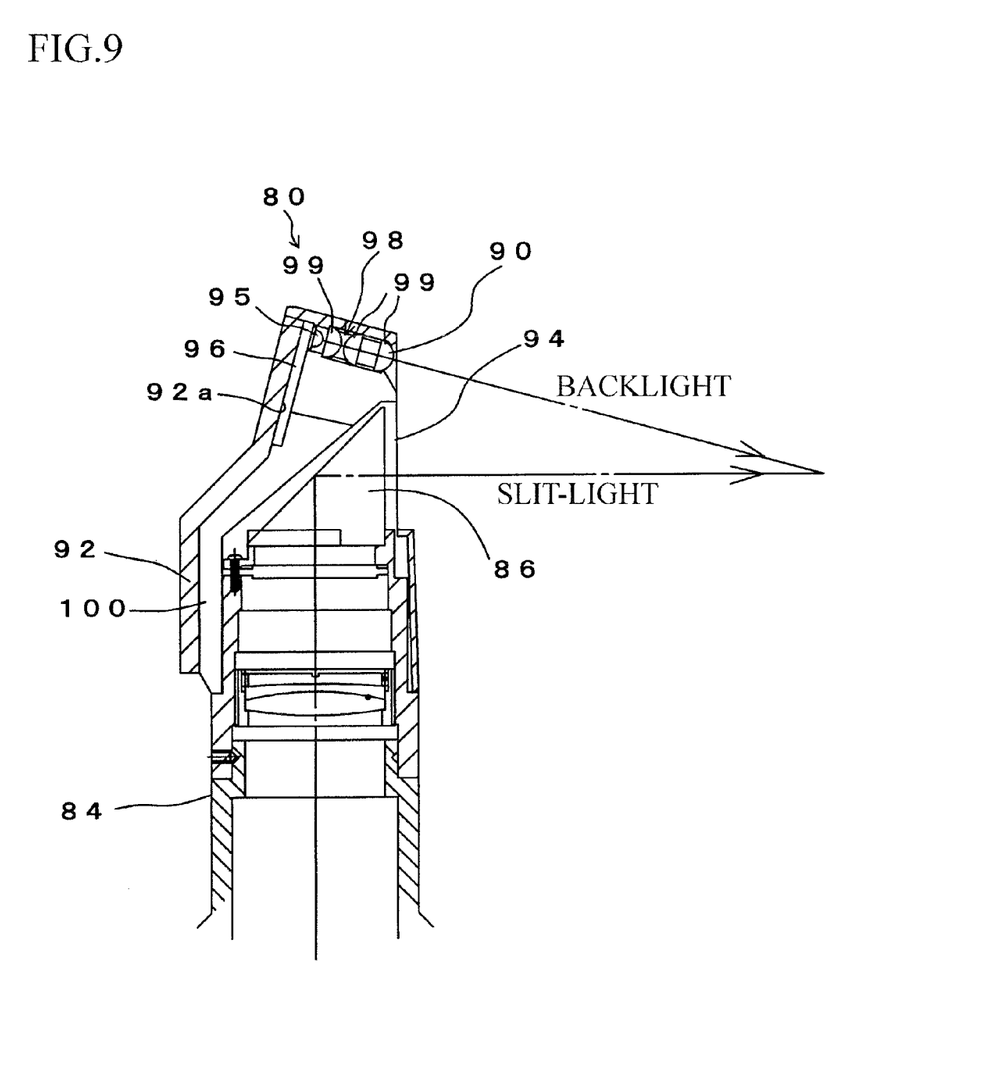
FIG. 9 is a left side view of a mirror unit of the slit lamp microscope of the second embodiment, which is seen from the examinee.

Next, a second embodiment of the slit lamp microscope of the present invention will be explained with reference to FIGS. 7-9. Note that, the structural elements described in the first embodiment are assigned the same numeric symbols and detailed explanation will be omitted.

In the slit lamp microscope 30 of the present embodiment, a slit lamp 82 is provided under a mirror unit 80. A slit-light upwardly emitted from the slit lamp 82 is horizontally reflected by the mirror unit 80.

The slit lamp 82 emits the slit-light in the horizontal direction. The slit lamp 82 is attached to a holding arm 84, which is extended in the vertical direction and formed into a cylindrical shape. A prism or a reflecting mirror (not shown) is provided in the holding arm 84. The slit-light emitted from the slit lamp 82 is reflected, so that the light path of the slit-light is changed vertically upward by the prism or the reflecting mirror in the holding arm 84.

The mirror unit 80 is attached to an upper end part of the holding arm 84. The mirror unit 80 includes a prism 86. The slit-light, which has been emitted vertically upward, is reflected in the horizontal direction by the prism 86 so as to irradiate the eye of the examinee. Note that, a reflecting mirror may be used, instead of the prism 86, so as to irradiate the eye of the examinee with the slit-light.

The mirror unit 80 includes not only the prism 86 for reflecting the slit-light but also a backlight source 90. The backlight source 90 is provided to irradiate the eye of the examinee with a backlight.

In the present embodiment, the backlight source 90 is provided above the prism 86. A light path of the backlight emitted from the backlight source 90 is inclined 28 degrees with respect to the horizontal plane, and the backlight is emitted toward the eye of the examinee from above.

Next, the detailed structure of the mirror unit 80 will be explained with reference to FIG. 9.

The mirror unit 80 has a metal chassis 92, in which the prism 86 is accommodated. A lower part of the chassis 92 is formed into a cylindrical shape. The cylindrical lower part of the chassis 92 covers the holding arm 84 so as to place on the holding arm 84.

A side face of the chassis 92, which faces the examinee, has an opening section 94, so that the prism 86 is exposed. The slit-light reflected by the prism 86 is emitted toward the eye of the examinee.

Note that, in case of reflecting the slit-light above the cylindrical holding arm 84 like the present embodiment, it is preferable to employ the prism, whose planar area is greater than that of a reflecting mirror, so as to prevent dusts, etc. from entering the holding arm 84.

The backlight source 90 is provided above the opening section 94 of the chassis 92, and the backlight is emitted toward the eye of the examinee through the opening section 94.

The backlight source 90 includes an LED board 96, on which an LED 95 is mounted, and a lens unit 98 having a plurality of lenses 99. The LED 95 emits the backlight. The lenses 99 are assembled in the lens unit 98.

A rear face of the LED board 96 is attached on an inner face 92a of a rear side wall (seen from the examinee) of the chassis 92. The backlight source 90 is accommodated in the chassis 92.

By accommodating the backlight source 90 in the chassis 92, heat generated in the LED board 96 can be conducted through the chassis 92 and released outside from an outer wall of the chassis 92. Therefore, the heat can be easily released without providing any heat-releasing means.

Further, a lead hole 100, through which lead lines extended from the backlight source 90 are introduced outside, is formed in a rear part (seen from the examinee) of the chassis 92. The lead hole 100 is formed in the vertical direction, so that the lead lines from the backlight source 90 can be extended along the holding arm 84. By extending the lead lines, on the rear side seen from the examinee, along the holding arm 84, an external view can be good.

Other Embodiments

In the mirror unit of the first embodiment, the backlight source is provided under the reflecting mirror. Further, in the mirror unit of the second embodiment, the backlight unit is provided above the prism.

However, in the present invention, the positional relationship between the reflecting mirror (or the prism) and the backlight source is not limited to the above described embodiments. Any other arrangements may be employed as far as the reflecting mirror (or the prism) and the backlight source are provided in the mirror unit.

For example, the reflecting mirror may be a semi-transparent mirror, and the backlight source may be provided in the mirror unit. With this structure, the backlight is emitted in the mirror unit and directed toward the eye of the examinee through the semi-transparent reflecting mirror, and the slit-light emitted from above is reflected on the reflecting mirror and directed toward the eye of the examinee.

Further, the light source of the backlight is not limited to the LED. Other light-emitting means may be employed.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention has been described in detail, it should be understood that the various changes, substitutions, and alternations could be made hereto without departing from the spirit and scope of the invention.

What is claimed is:

1. A slit lamp microscope, comprising:
  a slit lamp for emitting a slit-light;
  a mirror unit having a reflecting mirror or a prism, which reflects the slit-light emitted from the slit lamp toward an eye of an examinee;
  a microscope unit for observing the eye of the examinee; and
  a backlight source for emitting a backlight which illuminates a circumference of the slit-light, toward the eye of the examinee,
  wherein the mirror unit includes a metal chassis containing a holding section having a groove with a width which is nearly equal to a thickness of the reflecting mirror, the reflecting mirror being slidably received by the groove and clamped by the holding section,
  a spring member provided at the rear side of the reflecting mirror so as to press and fix the reflecting mirror in the holding section, without play, and
  the backlight source is provided in the metal chassis.

2. The slit lamp microscope according to claim 1, wherein the backlight source is provided in a lower part of the reflecting mirror or the prism of the mirror unit.

3. The slit lamp microscope according to claim 1, wherein the backlight source is provided in an upper part of the reflecting mirror or the prism of the mirror unit.

4. The slit lamp microscope according to claim 1, wherein an outer wall of the mirror unit is made of a metal, and
  heat generated by the backlight source can be released outside from the outer wall of the mirror unit.

5. The slit lamp microscope according to claim 2, wherein an outer wall of the mirror unit is made of a metal, and
  heat generated by the backlight source can be released outside from the outer wall of the mirror unit.

6. The slit lamp microscope according to claim 3, wherein an outer wall of the mirror unit is made of a metal, and
  heat generated by the backlight source can be released outside from the outer wall of the mirror unit.

7. The slit lamp microscope of claim 1, wherein the angle of the slit-light reflected by the reflecting mirror and the angle of the backlight are simultaneously adjusted by adjusting the angle of the mirror unit.

* * * * *